United States Patent [19]

Shafritz

[11] Patent Number: 4,562,159

[45] Date of Patent: Dec. 31, 1985

[54] DIAGNOSTIC TEST FOR HEPATITIS B VIRUS

[75] Inventor: David A. Shafritz, Larchmont, N.Y.

[73] Assignee: Albert Einstein College of Medicine, A Division of Yeshiva Univ., Bronx, N.Y.

[21] Appl. No.: 249,369

[22] Filed: Mar. 31, 1981

[51] Int. Cl.$^4$ .................... C12N 15/00; G01N 33/50
[52] U.S. Cl. .................... 436/501; 436/504; 436/804; 436/808; 436/810; 436/811; 436/815; 436/820; 435/6; 435/172.3; 435/235; 435/317; 435/948; 935/78; 206/569
[58] Field of Search .................... 424/1, 1.5; 435/41, 435/172, 174, 849, 948, 317, 4-8, 91, 240.6, 235-238; 23/230 B; 436/501, 63, 94, 804, 808-811, 820, 815, 504; 252/301.1; 536/27-29; 206/569; 935/76-79

[56] References Cited

U.S. PATENT DOCUMENTS

| | | |
|---|---|---|
| 4,034,072 | 7/1977 | Mjos et al. |
| 4,038,378 | 7/1977 | Khare |
| 4,139,346 | 2/1979 | Rabbani ........................ 422/56 |
| 4,237,224 | 12/1980 | Cohen et al. .................. 47/58 |
| 4,241,175 | 12/1980 | Miller et al. |
| 4,302,204 | 11/1981 | Wahl et al. ................... 422/56 |
| 4,358,535 | 11/1982 | Falkow et al. ................ 424/2 |
| 4,379,839 | 4/1983 | Spiegelman .................... 435/5 |
| 4,393,201 | 7/1983 | Curtis et al. ................. 536/27 |
| 4,395,486 | 7/1983 | Wilson et al. ................. 435/6 |
| 4,396,713 | 8/1983 | Simpson et al. ............... 424/253 |

FOREIGN PATENT DOCUMENTS

2043323  5/1980  United Kingdom.

OTHER PUBLICATIONS

Burrell, C. J. et al., Nature, vol. 279, pp. 43-47, (1979).
Galibert et al., Nature, vol. 281, pp. 646-650, (1979).
Charnay, P., Proc. Natl. Acad. Sci., vol. 76(5), pp. 2222-2226, (1979).
Pase K. M. et al., Nature, vol. 282, pp. 575-579, (1979).
Moseley et al., J. Infect. Disease, vol. 142(6), pp. 892-899, (1980).
Owens R. A. et al., Phytopathology, vol. 71(7), p. 770, (1981).
Brandsma et al., PNAS, vol. 77(11), pp. 6851-6855, (1980).
Kafator, F. C. et al., Nucleie Acid Research, vol. 7, (6), pp. 1541-1552, (1979).
Price, P. et al., J. Medical Virology, vol. 6, pp. 139-146, (1980).
PNAS vol. 77(11), pp. 6851-6855, (11-1980), Brandsma and Miller.
Shouval et al., Clinical Research, vol. 28, No. 2, Apr. 1980, (Abstract).
Chakraborty et al., Nature, vol. 286, No. 5772, pp. 531-533, Jul. 31, 1980.
Shouval et al., Proceedings National Academy of Science (PNAS), U.S.A., vol. 77, No. 10, pp. 6147-6151, Oct. 1980.
Bonino et al., Gastroenterology, vol. 79, No. 5, Nov. 1980, p. 1006.
Shafritz and Kew, Hepatology, vol. 1, No. 1, pp. 1-8, Jan.-Feb. 1981.
Williams et al., Journal of Virology, vol. 29, No. 2, Feb. 1979, pp. 555-575.
Science, vol. 196, pp. 172-174, 1977, Article, Armstrong et al.
Villa-Komaroff et al., Proc. Natl. Acad. Sci. USA, vol. 75, No. 8, pp. 3727-3731, Aug. 1978, Biochemistry.
Leder et al., Owner's Manual, Laboratory of Molecular Genetics, National Institute of Child Health and Human Development.
Clarke et al., Proc. Nat. Acad. Sci. USA vol. 72, No. 11, pp. 4361-4365. Nov. 1975, Biochemistry.
Valenzuela et al., Nature, vol. 280, Aug. 1979, pp. 815-819.
Sninsky et al., Nature, vol. 279, May 24, 1979, pp. 346-348.
Burrell et al., Nature vol. 279, May 3, 1979, pp. 43-47.
Cummings et al., Proc. Natl. Acad. Sci USA, vol. 77, pp. 1842-1846, Apr. 1980.
Blattner et al., Science, vol. 196, pp. 161-169, Apr. 8, 1977.
Proc. Natl. Acad. Sci. USA, vol. 75, No. 0, pp. 4533-4537, Sep. 1978, Summer et al.
Proc. Nat. Acad. Sci. USA, vol. 72, No. 11, pp. 4597-4601, Nov. 1975, Summers et al.
Chang et al., Journal of Bacteriology, Jun. 1978, pp. 1141-1156, vol. 134, No. 3.
Mertz et al., Proc. Nat. Acad. Sci. USA, pp. 3370-3374, Nov. 1972, vol. 69, No. 11.
Cohen et al., Proc. Nat. Acad. Sci. USA, vol. 70, No. 11, pp. 3240-3244, Nov. 1973.
Katz et al., Journal of Bacteriology, May 1973, pp. 577-591, vol. 114, No. 2.
Dingman et al., vol. 7, No. 2, Feb. pp. 659-668, (1968), Biochemistry.
Rigby et al., J. Mol. Biol. (1977) 113, 237-251.
Molec gen. Genet 145, 155-158, 1976, pp. 155-158.
Bethesda Research Laboratories, Inc., BRL Product Profile.
P. Leder et al., Science vol. 1, Apr. 8, 1977, pp. 175-177.
Grunstein et al., Biochemistry, vol. 72, No. 10, pp. 3961-3965, Oct. 1975.

Primary Examiner—Ben R. Padgett
Assistant Examiner—M. Moskowitz
Attorney, Agent, or Firm—Darby & Darby

[57] ABSTRACT

A method and test kit are disclosed for detecting the presence of hepatitis B virus in a test specimen containing at least a portion of the DNA of the virus. A test reagent comprises cloned hepatitis B virus-DNA that has been repurified by treatment with a restriction enzyme and labelled to high specific activity with a radioactive label. The sample to be tested is fixed to a solid matrix, incubated in the presence of the test reagent under hybridization conditions and detected by hybridization to the labelled DNA probe. The uncombined HBV-DNA (labelled) is removed from the substrate, and the hybridized HBV-DNA determined by scintillation counting or by autoradiography of the substrate.

36 Claims, No Drawings

DIAGNOSTIC TEST FOR HEPATITIS B VIRUS

BACKGROUND OF THE INVENTION

This invention pertains to a method and test kit for the detection of hepatitis B virus by nucleic acid hybridization. More specifically, the invention pertains to a method for detecting the presence of hepatitis B virus-DNA (hereinafter sometimes referred to as HBV-DNA) in the serum of a human or animal subject.

Still more specifically, the invention relates to a method for the direct detection of HBV-DNA in blood, blood products, vaccines, and other body fluids.

Over the years several tests have been employed to detect the presence of hepatitis B virus (hereinafter sometimes referred to as HBV) constituents in serum and other body fluids. These tests are primarily immunological in principle and depend on the presence of antibodies produced in humans or animals to detect specific viral proteins such as hepatitis B surface antigen $HB_sAg$), hepatitis B core antigen ($HB_cAg$) or hepatitis B "E" antigen ($HB_eAg$). Radioimmunoassay, considered to be the most sensitive immunological technique, employs 125 iodine-labelled antibody. Radioimmunoassay has sufficient sensitivity to detect nanogram ($10^{-9}$ gram) quantities of $HB_sAg$. However, immunological tests are indirect, and nonspecific antigen-antibody reactions do occur resulting in false positive determinations. Furthermore, in certain instances the antigen-antibody tests are negative in donor serum, but the recipient of transfused blood develops hepatitis B virus infection. Despite careful radioimmunoassay of all blood donated in the U.S. for $HB_sAg$, a significant percentage of post-transfusion hepatitis cases are still caused by transfusion of blood that is contaminated with HBV which eluded detection. Hence, radioimmunoassay and other immunological tests have serious drawbacks, limited utility and provide only an indirect index of potential viral infectivity.

Among the other tests used to identify potentially infectious virus in serum are the viral polymerase assay and electron microscopy. For the most part, these methods are cumbersome assays of relatively low sensitivity and would be impractical for use as a routine laboratory screening procedure.

The present invention involves the discovery of a simple and sensitive mass screening procedure for hepatitis B virus in which molecular hybridization and recombinant DNA techniques are used to detect HBV-DNA directly in human serum. According to the invention, a hybridization probe is prepared by cloning hepatitis B virus-DNA. The cloned HBV-DNA is purified from the recombinant plasmid and labelled to high specific activity with $^{32}P$ or $^{125}I$ to form a hybridization probe. The hybridization probe is applied to a test sample (suspected of containing HBV) that has been fixed to a suitable substrate and the probe bearing sample incubated under hybridization conditions which permit the labelled HBV-DNA to hybridize (combine) with only HBV-DNA sequences present in the test sample. Following incubation, the uncombined HBV-DNA probe is removed from the substrate and the presence of hybridized HBV-DNA determined by liquid scintillation spectroscopy or by autoradiography of the substrate. A positive assay is evidence that the test sample contains the DNA of HBV.

This hybridization analysis is substantially more sensitive than methods presently utilized to detect HBV or HBV proteins in the serum or other body fluids. Moreover, the test provides direct evidence for viral infectivity by identifying the DNA of the viral particle, rather than by demonstrating the presence of viral protein antigens. The test is highly specific for HBV, virtually eliminates false positive results and can be applied to other DNA or RNA test systems for which a purified nucleic acid hybridization probe can be prepared. A principal advantage of the method of the present invention is that the sample to be tested can be used directly, without significant pretreatment. The components required to conduct the assay of the invention can be prepared in the form of a test kit, which can be utilized without difficulty by laboratory personnel with a minimum of training.

It is therefore an object of the present invention to provide a method for the detection of HBV in serum, or body fluids.

A further object of the present invention is to provide a sensitive mass screening method for the detection of HBV by demonstrating the presence of the unique DNA contained within this virus.

A still further object of the invention is to provide a method for identifying carriers of HBV who may elude detection by other tests.

A further object of the invention is to provide a simple test to distinguish individuals who have only viral proteins in their serum or body fluids from those patients who manifest potentially complete infectious virus as demonstrated by the presence of HBV-DNA.

Another object of the invention is to provide a method for assaying the level of infectious HBV-DNA in a patient's peripheral circulation or body fluids.

Another object of the present invention is to provide a test kit comprising an HBV-DNA hybridization probe, a detection substrate, and a sealable container for incubating the test reagents, and optionally the other components necessary to conduct the test; namely, incubation solutions.

References which pertain to the subject invention are:

Shouval et al., Clinical Research, Volume 28, No. 2, April 1980 (Abstract);

Chakraborty et al. Nature, Volume 286, No. 5772, pages 531-533, July 31, 1980.

Shouval et al., Proceedings National Academy of Science (PNAS) U.S.A., Volume 77, No. 10, pages 6147-6151, October 1980.

Bonino et al., Gastroenterology, Volume 79, No. 5, November 1980, page 1006.

Shafritz and Kew, Hepatology, Volume 1, No. 1, pages 1-8, Jan.-Feb. 1981.

U.S. Pat. No. 4,034,072.

U.S. Pat. No. 4,038,378.

DETAILED DESCRIPTION OF THE INVENTION

The present invention is based on the fact that the genetic information or code of a specific virus comprises a nucleic acid which may be composed of a polymer of ribonucleotides (RNA) or deoxyribonucleotides (DNA). HBV is a DNA virus. It is known that nucleotide molecules that are complementary to one another can interact in solution by "hydrogen-bonding" to form stable base pairs. Thus, adenine recognizes thymidine and quanine recognizes cytosine. When two single-stranded, complementary, DNA molecules are present in a solution under conditions in which the complementary nucleotides can recognize one another, these molecules will interact to form a stable duplex structure. This duplex is resistant to attack by certain nucleases which totally degrade single-stranded DNA. It is therefore possible to ascertain with great precision the extent of duplex formation. This interaction of base sequences in polynucleotides reacting in solution is referred to as "reannealing" or "molecular hybridization" and can be performed under specific conditions in which false interactions do not occur.

According to the present invention, a specific double-stranded DNA sequence (HBV-DNA) is isolated, amplified by cloning, purified to homogeneity and labelled with a detectable marker. The purified labelled DNA is denatured (e.g. by boiling at 100° C.) to separate it into two single strands and is added to a test solution containing denatured nucleic acid from a sample to be tested. The aqueous conditions of the solution (ionic strength, polarity, pH and temperature) are adjusted to allow nucleic acid reannealing (rejoining). In this manner the labelled molecules can associate with their unlabelled counterparts. Thus, the labelled, purified HBV-DNA will associate with hepatitis B viral sequences in the test solution. The purified DNA probe can be radioactively labelled in vitro to high specific activity ($2-4 \times 10^8$ counts per minute (CPM) per microgram DNA), permitting the test to detect picogram ($10^{-12}$ gm) quantities of DNA in a test sample. Thus, on a weight comparison basis, the present technique for HBV-DNA detection is approximately $10^3$ times more sensitive than radioimmunoassay, the technique heretofore used to detect HBV protein antigens.

In a preferred embodiment, the invention is adapted to the detection of hepatitis B virus DNA sequences in serum, or in other peripheral body fluids using a test kit consisting of a test reagent comprising purified, cloned hepatitis B virus DNA, a substrate for retaining a sample of the patient's serum to be affixed during the test and a container for incubating the substrate during the hybridization reaction. In operation, the reagent is prepared by cloning hepatitis B virus DNA. The HBV-DNA is then purified from a recombinant plasmid with a restriction enzyme by a two-step procedure consisting of (1) treatment of the recombinant plasmid with a restriction enzyme to break the recombinant DNA into its component parts, and (2) reisolating the HBV-DNA sequence using conventional molecular weight separation techniques. The purification step has been found to be of great importance as a means for avoiding false positive assays. In the preferred embodiment, the purified HBV-DNA is labelled to high specific activity, preferably with radioactive $^{32}P$ or $^{125}I$. A serum sample is collected from the patient and fixed on a substrate (preferably a nitrocellulose filter). The radioactively labelled HBV-DNA hybridization probe is brought into contact with the sample on the filter and the filter incubated in a sealed container in the presence of a hybridization solution under hybridization conditions.

The hybridization solutions employed in the invention may be either aqueous or partially organic (hydrophobic or "non-aqueous"). The aqueous hybridization solution is of approximately neutral pH, contains salts to adjust ionic strength, denatured carrier DNA, and Denhardt's solution to prevent nonspecific sticking of denatured or single-stranded DNA to the filter. An ionic detergent (e.g. sodium lauryl sulfate) is also present in the range 0.1 to 0.5% W/V.

Incubation is generally performed at 65°–70° C. for a period of 12–36 hours.

The preferred hybridization pH conditions are approximately neutral pH, although a pH value in the range from pH 6.5 to pH 8.0 has been found to give satisfactory results.

Hybridization is conducted at a predetermined temperature which is approximately 10° C. below the melting temperature of the hybrid for aqueous conditions. The melting temperature of the hybrid in partially organic solutions is somewhat lower and therefore the range of temperatures in which hybridization is conducted is reduced to 5°–7° C. below the melting temperature of the hybrid. In most instances temperatures in the range of between about 65° and 70° C. (preferably 65° C.) for aqueous, and between about 40°–45° C. have been found to be effective for partially organic hybridization solutions (preferably 42° C.) at relatively high ionic strength.

For stable polynucleotide hybrids to form under the conditions of the test, a minimum length of approximately 200 nucleotides is required. Therefore, any portion of the HBV genome 200 nucleotide base pairs or longer up to 3200–3300 base pairs of the full length HBV genome can be cloned, isolated, purified and used as a hybridization probe.

In general, hybridization is conducted for a predetermined time between about 8 and about 36 hours. The duration of hybridization is not critical. Longer hybridization reaction times are not harmful, and generally afford more complete hybridization. At the conclusion of the hybridization period, the radioactive waste solution is discarded, the filter is removed from the sealed container and washed to remove any uncombined HBV-DNA (labelled). After drying, the filter is cut into sections for liquid scintillation counting, or the entire filter sheet may be exposed to autoradiography overnight at low temperature (between −60° to about −86° C. is satisfactory). Positive samples (containing HBV-DNA) are evident by retention of radioactive counts on the filter. If autoradiography is employed, positive samples are detected on developed x-ray film as black (darkened) circular spots in the same positions in which test samples were originally applied.

Hepatitis B virus is a DNA virus and may be identified by electron microscopy in the serum of acutely infected individuals or chronic hepatitis B carriers as 42 nanometer spheres, often referred to as "Dane" particles. The outer shell of the virus contains hepatitis B surface antigen ($HB_sAg$) and the inner core or nucleocapsid (approximately 27 nanometers) contains hepatitis B core antigen ($HB_cAg$), as well as other viral proteins including hepatitis B "E" antigen, and hepatitis B virus-DNA (HBV-DNA). Although HBV-DNA is circular and double-stranded, one strand (the b strand) is incomplete, while the other (the a strand) is complete but "nicked" (complete but not covalently closed). The incomplete strand lacks between 15 and 45 percent of its sequence complement. Robinson, Ann. Rev. Microbiol. 31, 357–377 (1977); Summers et al., Proceedings of the National Academy of Sciences, U.S.A. 72, 4597–4601 (1975). A unique polymerase (viral polymerase), found in the inner core of the virus, adds deoxyribonucleotides to the incomplete b strand. This reaction completes the double-stranded circle and is useful in preparing full length, double-stranded, HBV-DNA for cloning in bacterial plasmids or bacteriophage lambda.

The high specific radioactivity levels employed in practicing the preferred embodiment of the invention are capable of detecting HBV-DNA sequences in a mixture of DNA species at concentrations of less than one molecule HBV-DNA per million molecules of other DNA species or, less than 0.1 copy per human genome equivalent. Under these circumstances, it has been found that HBV-DNA, as obtained from Dane particles in human serum, is not satisfactory for use as a molecular hybridization probe in the invention. The Dane particle HBV-DNA contains a significant percentage of "impurities" that have been found to yield false positive reactions under certain conditions. Accordingly, an important aspect of the invention involves the use of totally purified HBV-DNA sequences as the molecular hybridization probe. Purification of the HBV-DNA sequence is achieved by preparing a recombinant plasmid or bacteriophage molecule containing HBV-DNA, infecting appropriate bacterial cells with this combinant vector to produce many copies of the recombinant molecule, reisolating the recombinant HBV-DNA containing plasmid (or lambda phage) in large scale and thereafter repurifying the HBV-DNA sequence from the recombinant DNA molecule. Use of purified HBV-DNA has also been found to be especially critical, because the present test procedure employs crude serum specimens which are directly fixed to a substrate (e.g. a nitrocellulose filter) without prior DNA extraction, electrophoresis or equivalent purification.

The preferred procedure for cloning HBV-DNA for use in the present invention is that described by Cummings et al. in Proceedings of the National Academy of Science U.S.A. 77: 1842–1846, 1980, whose disclosure is incorporated herein by reference.

Alternate cloning procedures that employ other plasmid or bacteriophage vectors (and which are also satisfactory for use in the present invention) are described in the literature (See for example, Burrell, et al., Nature 279: 43–47, 1979: Charnay, et al. Proc. Natl. Acad. Sci. U.S.A. 76: 2222–2226, 1979; Sninsky, et al. Nature 279: 346–348, 1979 and Valenzuela, et al. Nature, 280: 815–819, 1979. In the cloning procedure, Dane particles containing HBV-DNA are concentrated from 5–10 ml of human serum by ultracentrifugation at 105,000 times gravity overnight. To complete the b strand of Dane particle DNA and extract fully double-stranded HBV-DNA for cloning, the procedure of Summers, et al. Proc. Natl. Acad. of Sciences U.S.A. 75: 4533–4537, 1978 (whose disclosure is incorporated herein by reference) is employed. Pelleted virus particles are resuspended in 100 microliters of polymerase reaction buffer (0.1M Tris HCl, pH 8.0, 20 mM $MgCl_2$, 0.5M NaCl, 0.2 mM each of dATP, dGTP, dCTP and dTTP, 1 mM dithiothreitol and 0.1% Triton X-100 (Rohm and Haas, Philadelphia, PA). The polymerase reaction is initiated by incubating the suspended viral particles at 37° C. for two hours. The reaction is halted by adding 50 microliters ($\frac{1}{2}$ volume) of a solution containing 10 mM Tris HCl, pH 7.4, 10 mM EDTA, 0.2% sodium lauryl sulphate (SDS) and 0.5 mg per ml of pronase to the reaction vessel. All viral proteins and contaminating human proteins are digested by incubating the solution at 37° C. for two hours. The nucleic acid content of the incubation mixture is isolated by extraction with phenol to remove residual protein and fully double-stranded HBV-DNA precipitated out in ethanol. The fully double-stranded HBV-DNA is then linearized by treatment with restriction endonuclease EcoR1 (New England Biolabs, Beverly, Mass.), which produces a single break in each strand of HBV-DNA at the hexanucleotide sequence;

5'-G ↓ AATTC-3'

3'-CTTAA ↑ G-5'

The DNA is incubated at 37° C. for six to twelve hours using one unit of Eco R1 restriction enzyme per microgram of DNA in a buffered solution containing 100 mM Tris HCl, pH 7.5, 50 mM NaCl, and 5 mM $MgCl_2$.

The linearized HBV-DNA is now ready to be joined to a bacterial plasmid or a bacteriophage. The plasmids preferred for use in the present invention are identified as pAO1 (as described in Cummings, et al. Proc. Natl. Acad. Sci. USA 77-1842–1846, 1980) and pBR322 (as described in Bolivar et al; Gene 2, 95–113 (1977) (incorporated herein by reference). pAO1 is a plasmid which confers kanamycin reistance to bacterial cells in which it is replicating. It is prepared from plasmid pCR1 which was originally described by Covey et al in Molec. Gen. Genetics 145: 155–158 (1976) (incorporated herein by reference). pCR1 is a 8,700 base pair plasmid. pAO1 contains a small deletion between the two Pst1 sites of pCR1 and is produced by digesting pCR1 with restriction enzyme pstI and reannealing. Plasmid pAO1 functions in an identical fashion to pCR1, but has the advantage of having only one residual Pst1 site. This plasmid also has one EcoR1 site which can be used for insertion of HBV-DNA. Bacteria transformed by pAO1 can be selected by kanamycin resistance and recombinant clones can be tested for the present of HBV-DNA sequences by standard techniques (Grunstein and Hoagness, Proc. Natl. Acad. Sci. U.S..A. 72:3961–3965 1975). For the purposes of this invention, pAO1 has the advantage that it is a relatively large plasmid and can be easily separated from HBV-DNA sequences in recombinant molecules. A more frequently used plasmid for cloning of HBV-DNA is plasmid pBR322. This plasmid also contains a single EcoR1 site (or a single Pst1 site) which can be used for insertion of similarly restricted HBV-DNA. An advantage is that pBR322 is commercially available (Bethesda Research Laboratories Inc., Bethesda, Md.), but its size (4380 base pairs) is relatively close to that of full-length HBV-DNA (3200–3300 base pairs), and it is more difficult to separate these components and repurify HBV-DNA after cloning and amplification. Plasmids pACYC184 (Chang and Cohen; J. Bact, 134, 1141–1156 (1978); PCR1 (Covey et al, Molec. Gen. Genetics 145: 155–158, 1976), and many others are also suitable for use in the invention. Instead of a plasmid, a bacteriophage including for example, Charon (Blattner et al Science 196: 161–169, 1977) or Lambda gt Wes. Lambda B Series (Leder et al Science 196: 175–177, 1977; the teachings of the preceding articles are incorporated herein by reference) may be employed. Both of these bacteriophages are commercially available from Bethesda Research Laboratories, Inc., Rockville, Md. In the present procedure, a plasmid (e.g.pAO1 or pBR322) is cleaved with a restriction enzyme (e.g. EcoR1). Methods of cleavage with restriction enzymes are described in Greene et al. Methods in Molecular Biology, Vol. 9, Ed. Wickner, R. B. (Marcel Dekker Inc., New York), DNA Replication and Biosynthesis", Mertz and Davis, Proc. Natl. Acad. of Science, U.S.A., 69, 3370 (1972). The bacterial plasmid (e.g. pAO1 or pBR322) may be treated with Eco R1 to produce overlapping break points ("sticky ends") with the same sequence as in the Eco R1 treated HBV-DNA. The two DNA's are annealed together to form chimeric hybrids (recombinant DNA) according to a modification of the procedure of Clark, L. and Carbon, J.; Proc. Natl. Acad. of Science U.S.A., 72: 4361-4365, 1975. In this procedure, equimolar amounts of Eco R1 (restriction enzyme), linearized HBV and plasmid DNAs being used for constructing the recombinant are mixed together in a solution of 10 mM Tris HCl, pH 7.4, 100 mM NaCl, and 1 mM EDTA. The solution is incubated successively at 55° C. for one hour, 46° C. for one hour, 37° C. for one hour and finally at room temperature for between two and four hours. The hybrid molecules are covalently sealed together with an in vitro ligation reaction, using $T_4$DNA ligase, although this step is not essential. Endonuclease digestion is normally carried out at moderate temperatures (in the range between about 20° and 40° C.) in an appropriately buffered aqueous medium, generally at a pH of between about 6.5 to 8.5). The total DNA content in the reaction mixture will generally be between about 0.1 to 1.0 ug per ml. The time required for the reaction is variable, and can range from a few minutes to several hours, depending on the ratio of enzyme to DNA. An excess quantity of endonuclease is generally employed for the restriction reaction, and usually comprises between about 5–10 units of restriction endonuclease for each 10 micrograms of DNA for an incubation time of 6–12 hours. After reannealing of the linearized plasmid and HBV-DNA, the recombinant HBV-DNA molecule is then amplified in bacteria cells by well-established transfection procedures. In general, *E. Coli* derivatives of the K12 series (e.g. HB101, C600, $_x$1776 etc.) are used for cloning in the present invention, although other bacteria may be suitably employed provided they can be transformed. Preferably, 1 microgram of recombinant plasmid HBV-DNA is incubated at 37° C. for 20 minutes with $1 \times 10^7$ competent bacteria (*E. Coli*) in a 100–300 microliter reaction mixture containing 20 mM Tris HCl pH 8.0, 20 mM NaCl and 1.0 mM EDTA. Various modifications of this transformation procedure have developed, but they all follow the essential steps outlined by Cohen et al. in Proc. Natl. Acad. of Science U.S.A. 70: 3240-3244 (1973). Another useful transformation protocol is that described by Villa-Komaroff et al, Proc. Natl. Acad. of Sci., USA 75: 3727-3731 (1978).

The transfected bacteria cells are plated on 1.0% agar dishes in Luria broth (L-broth) which contains salts, glucose, protein hydrolysate, minerals and other nutrients, using an antibiotic selection feature corresponding to the specific plasmid vector utilized (the antibiotic kanamycin is used for plasmid pAO1, while ampicillin and/or tetracycline is conventionally used in the case of plasmid pBR322). The composition of L-broth agar plates per Liter of medium is 10 gm Bactotryptone; 5 gm Bacto yeast; 10 gm Brain Heart Infusion; 10 gm NaCl; 0.8 gm glucose. Individual recombinant clones containing HBV-DNA are isolated and grown in large scale (1–5 L) in L-broth suspension culture, using chloramphenicol amplification.

Recombinant plasmid HBV-DNA is then reisolated by the detergent lysis "cleared-lysate" procedure taught in Katz, et al., J. Bacteriol.114: 557–591, 1973. In this procedure, bacteria are harvested by centrifugation at $800 \times g$, and treated with a solution containing 1 mg per ml of lysozyme and 30–40 mM EDTA to digest the bacterial cell wall. Triton X-100 is added to a final concentration of between 1–5% by volume to lyse the bacteria and the solution is again centrifuged at 30,000 RPM in a Sorvall centrifuge for one hour at 4° C. to pellet cell debris and chromatin. The plasmid DNA remains in the supernatant fraction and is collected. The plasmid is purified by banding in a cesium chloride gradient for 48 hours. The plasmid band is identified by ethidium bromide fluorescence and is removed by puncturing the side wall of the centrifuge tube with a needle and withdrawing the fluorescent plasmid material under direct vision using a syringe. Material from the gradient is extracted with isopropanol saturated with cesium chloride, dialyzed for between 12–24 hours to remove the cesium chloride, extracted with phenol and precipitated with ethanol.

HBV-DNA is reisolated from the cloning vector by treatment with the restriction endonuclease Eco R1, using one unit Eco R1 per microgram of DNA in a buffered solution containing 100 mM Tris HCl, pH 7.5, 50 mM NaCl, and 5 mM of $MgCl_2$. As Eco R1 is capable of recognizing the sites at which HBV-DNA has been inserted into the plasmid (or the lambda phage) vector, it will break the recombinant DNA into its original component parts.

The HBV-DNA portion is then reisolated and purified to a single molecular species of 3,250 nucleotide base pairs length by sucrose gradient centrfiguration and/or preparative agarose gel electrophesis. In the preferred procedure, 50 microgram aliquots of Eco R1 treated recombinant plasmid HBV-DNA are layered over 5 ml, 10 to 30 percent sucrose gradients under mineral oil in a solution containing 10 mM Tris HCl, pH 7.4, 100 mM NaCl and 1 mM EDTA and centrifuged at 38,000 rpm in a Beckman SW41 rotor for 16-20 hours. Fractions of 0.25 ml are collected from the bottom of the gradient tube using a peristaltic pump. The ultraviolet adsorbance of the effluent stream is monitored continuously at 260 nanometers with a conventional UV monitor. The heavier polynucleotide chain (i.e. the plasmid component which contains approximately 8,700 base pairs) elutes first from the gradient and the shorter length HBV-DNA segment (3,250 base pairs) elutes thereafter. The gradient fractions containing the HBV-DNA bands are pooled, precipitated in 2.5 volumes of ethanol, redissolved in a small volume of TE buffer (10 mm Tris HCl, pH 7.4; 1 mm EDTA) and subjected to electrophoresis on a 0.8%, 5 millimeter thick agarose slab gel. 10 to 20 micrograms of DNA is applied to each slot on the gel. Suitable buffers for the electropheresis include "E" buffer (40 mm Tris HCl, pH 7.8, 20 mM sodium acetate and 1 mM EDTA), or "P and D" buffer (as disclosed by Dingman and Peacock, Biochemistry 7: 659–667, 1968). Electrophoresis for 8 to 10 hours at 50 volts has been found to be generally sufficient for separating HBV-DNA from residual bacterial cell and plasmid DNA molecules. One microgram of ethidium bromide per ml of buffer is used in preparing the agarose gel. Ethidium bromide fluorescence at 260 nanometers of ultraviolet light is used to follow the migration of DNA and locate the position of HBV-DNA bands in the gel. HBV-DNA is eluted from the gel by slicing out the portion containing this band, placing it in a small amount of buffer in a dialysis bag and subjecting the cut out gel to electroelution at 200 volts for 30–60 minutes at room temperature in a solution containing 0.6 gm Tris base plus 200 ul glacial acetic acid in 1 liter of $H_2O$.

The purified HBV-DNA is labelled by in vitro incubation with $^{32}P$ or $^{125}I$ deoxyribonucleotides of very high specific radioactivity in the presence of bacterial enzymes DNase and polymerase I. These enzymes permit labelled deoxyribonucleotides to replace or substitute for unlabelled nucleotides in double-stranded DNA. This enzymatic reaction, referred to as "nick translation" (reference: Rigby, et al, Journal of Molecular Biology 113: 237–251, 1976), routinely yields labelled $^{32}P$ DNA's with a specific activity between about 200 counts per minute per picogram ($10^{-12}$ gram) DNA when $^{32}P$ dCTP and $^{32}P$ dGTP (400 to 800 Ci/m mole) are used as substrate along with unlabelled dATP and dTTP. Because standard autoradiographic and liquid scintillation spectroscopy techniques easily detect 50 counts per minute of $^{32}P$ radioactivity, and the background radioactivity for the hybridization method of the invention is extremely low (i.e. less than 10 counts per minute), the lower limit of sensitivity for the detection test of the invention is between about 0.1 and 0.5 picograms of hepatitis B virus DNA. Other detection labelling systems for use in the present invention include by way of example bioluminescent labels, microsphere agglutination techniques and fluorescence techniques.

The purified, labelled HBV-DNA prepared above is stored in a sealed container, in the refrigerator (2° C.) for use in the invention.

In carrying out the HBV-DNA assay of the invention, the labelled HBV-DNA is reacted directly with a test sample (e.g. a patients' serum, or other peripheral body fluid) that has been affixed to a solid matrix. Suitable matrices for use in the invention include nitrocellulose filter paper (preferably 0.2 or 0.45 micron pore size, commercially available from Millipore Corporation, Bedford, Mass., or Schleicher and Schuell Inc., Keane, N.H. Although nitrocelluose papers are preferred, the invention is not limited to use with this substrate. Almost any substrate or matrix material in the form of a sheet, bead or web to which DNA or RNA adheres (for example diazo benzyloxymethyl-cellulose paper (DBM paper) as described in U.S. Pat. No. 4,139,346) may be used as a substrate material in practicing the process of the present invention.

In conducting the hybridization test of the invention, it is necessary to incubate the test sample and the DNA probe under specific hybridization conditions in the presence of a hybridization medium as described herein. To prevent loss of fluid during heating operations as well as the loss of reactants and to prevent contamination, it has been found desirable to conduct the incubation in a container. The container should be constructed of a material that can withstand boiling. It is desirable that the container be of a sealable design but otherwise its configuration is not crucial. If the container is a plastic bag, it is preferable that the bag be made of a heat sealable material. In one preferred version of the invention, the matrix or substrate in which the reaction is conducted, is incubated in a small flexible heat-sealable plastic bag. It is generally desirable that the bag be of a flexible construction to permit most of the air in the bag to be forced out prior to sealing. Although it is not a requirement of the invention that the test be conducted under anaerobic conditions, the incubation solution may contain bubbles whose presence has been found to have an adverse effect by interfering with hybridization or creating high background areas on the filter and these bubbles are substantially eliminated when the air is forced out of the incubation bag.

The test procedure is simple and relatively straight forward. A sample of blood is collected by venipuncture or finger stick and is allowed to clot at room temperature. The serum is separated by routine clinical centrifugation and is used immediately or stored, in the frozen condition at a temperature between about −10° C. and −80° C. (preferably −70° C.) for later testing. Any aqueous solution, suspected to contain HBV-DNA, may be used as the sample to be assayed with the present test. However, in preparations where the HBV present content may be relatively low, it has been found desirable to concentrate the virus particles by ultra-centrifugation at 100,000×g or more for between 2 and 4 hours to sediment viral particles. The viral particles are thereafter suspended in a solution containing 10 mM Tris HCl, pH 7.4 and 100 mM NaCl.

A small serum specimen is applied as a circular spot to the nitrocellulose filter sheet or other matrix described above. This can be accomplished by directly spotting 5–10 microliter aliquots to the filter sheet or by applying up to 200 microliter of alkalinized serum (0.1–0.2M NaOH) or serum to which 0.1 to 0.5% sodium lauryl sulfate; 0.5 to 1.0M NaCl had been added and the sample warmed to 37° C. for 5–10 minutes. These samples are then filtered onto nitrocellulose, using a multichamber filtration apparatus. Nitrocellulose filter sheets (measuring 12 centimeters by 12 centimeters) may be divided into 100 sections (area 1.2 cm$^2$) to enable up to 100 serum specimens to be tested simultaneously on the same sheet. This permits the inclusion of many samples including positive and negative controls in the same test.

The matrix is air dried, saturated with the buffered solution and dried again in a vacuum oven at temperature between about 20° C. and 37° C. The filter matrix is then immersed in an enzyme solution which digests all protein, while leaving the nucleic acid fixed to the filter. The immersion should be for a period between about 30 to 120 minutes at 37° C. After protein digestion, the spot to which the serum specimen was fixed, usually becomes invisible. Suitable protein digestion agents include the enzymes pronase or proteinase K in an aqueous solution of 0.3M NaCl and 0.03M sodium citrate. Preferably, this solution will contain about 100–200 micrograms per ml of the protein digestion enzyme. The matrix is then washed carefully to remove all traces of the protein digestion enzyme. The washing step is generally conducted in a mild salt solution (e.g. 100 to 200 ml of an aqueous solution of 0.3M NaCl and 0.03M sodium citrate). After drying, the filter matrix is placed in a sealable container (e.g. a heat sealable plastic bag) which can withstand boiling water temperature. A quantity of an aqueous or partially organic pre-hybridization solution is added to the bag. Tables 1 and 2 below identify the formulas of two representative aqueous and partially organic pre-hybridization solutions that may be employed in practicing the present invention.

TABLE I

| Aqueous Prehybridization Solution (4 × SSC) |
| --- |
| 0.6 M NaCl |
| 0.06 M sodium citrate (pH 7.0) |
| 0.1% polyvinylpyrolidone (PVP) |
| 0.1% Ficoll |
| 0.1% bovine serum albumin (W/V) |
| 0.1% sodium lauryl sulfate (W/V) |
| 0.3 mg per ml denatured calf thymus |

TABLE I-continued

Aqueous Prehybridization Solution (4 × SSC)

(or salmon sperm) DNA

TABLE II

Partially-Organic Prehybridization Solution (5 × SSC)

50% deionized formamide (V/V)
0.75 M sodium chloride
0.075 M sodium citrate (pH 7.0)
0.1% bovine serum albumin (W/V)
0.1% Ficoll
0.1% polyvinylpyrolidone
25 mM sodium phosphate (pH 6.5)
0.1% sodium lauryl sulfate (W/V)
0.3 mg per ml denatured calf thymus
(or salmon sperm) DNA
1% glycine (W/V)

The hybridization solutions that are used in the present invention subsequent to the prehybridization solution have essentially the same constituents and percentage composition as the latter; but in the hybridization solutions the concentration of Ficoll, polyvinylpyrolidone and albumin are reduced to 0.02%, 0.02%, and 0.02%, respectively. Also, up to 10% sodium dextran sulfate may be added to the hybridization solution to accelerate the hybridization and to insure full hybridization within 8–12 hours. It is important that the hybridization solution used in the present invention be adjusted to fall within limits of ionic strength, pH, polarity and temperature to obtain adequate and satisfactory hybridization. Ionic strength of the prehybridization and hybridization solution (aqueous and partially organic) should be in the range of between 3×SSC to 6×SSC. SSC is an abreviation of standard for sodium chloride-sodium citrate solution. The standard medium (1×SSC) is a solution containing 0.15M sodium chloride; 0.015M sodium citrate at pH 7.0.

The ionic strength requirements for the hybridization solution are met, if the solution is between 3 and 6 times SSC and preferably 4–5×SSC. 5×SSC is a solution containing 0.75M sodium chloride; 0.075M sodium citrate at pH 7.0. Polyvinylpyrolidone and Ficoll and sodium lauryl sulfate (or other ionic detergents) may be added to the prehybridization and hybridization solutions for the purpose of preventing non-specific sticking of denatured labelled DNA to the filter. The partially organic hybridization solution is substantially identical to the aqueous solution, but contains approximately 50% by volume of deionized formamide and 1.0% by weight of glycine. As the percentage composition of formamide is increased, the melting temperature of the hybrid decreases, so that at approximately 50% formamide the preferred hybridization temperature is 42° C. Denhardt's solution (Denhardt, Biochem. Biophys. Res. Commun. 23: 641–646, 1966) is included in the preferred hybridization solution to prevent non-specific sticking of denatured or single stranded DNA to the filter (Denhardt's solution comprises 0.02% polyvinylpyrolidone (PVP) (avg. m.w. 360,000 and available from Sigma, St. Louis, Mo.,); 0.02% Ficoll (avg. m.w. 400,000 and available from Pharmacia Fine Chemicals, Parsippany, N.J.); and 0.02% bovine serum albumin (BSA). The denatured calf thymus or denatured salmon sperm DNA is present (0.15 to 0.5 milligrams/ml DNA) in the prehybridization solution as a carrier to keep all of the labelled hybridization probe in solution and to prevent non-specific sticking of denatured labelled DNA to the filter.

The bag containing the prehybridization solution and matrix is sealed and incubated at a temperature of about 65° and 70° C., preferably 65° C., for between about 4 to 6 hours, or overnight (preferably 6 hours). The prehybridization solution is removed and replaced with a fresh hybridization solution (aqueous or non-aqueous) plus an aliquot of the labelled purified HBV-DNA probe (approximately $1-2\times10^7$ cpm, or about 0.1 microgram DNA) which has been pretreated by boiling at 100° C. for between 5 and 10 minutes and rapidly cooled on ice just prior to use. A hybridization solution in which the concentration of polyvinylpyrolidone, Ficoll and albumin are reduced to between about 0.02% and 0.04%, and preferably to 0.02%, 0.02% and 0.02%, respectively, is added. The hybridization (incubation) container is resealed and incubated overnight or up to 48 hours at a temperature of between 65° C. and 70° C., preferably 65° C., for aqueous hybridization conditions and between about 37° C. and 45° C., and preferably 42° C. for partially organic (formamide) conditions.

After incubation, the radioactive waste solution is discarded, the filter removed from the bag and washed. A suitable washing solution contains 0.3M sodium chloride; 0.03M sodium citrate; and 0.1% sodium lauryl sulphate. This washing is conducted at room temperature. The washing operation is repeated twice with 0.015M NaCl; 0.0015M Na citrate; 0.1% sodium lauryl sulphate at elevated temperature, generally between 50° C. and 68° C., preferably 60° C. for 30 minutes each.

After air drying, the filter matrix is cut into sections for liquid scintillation spectroscopy, or the entire sheet may be exposed to autoradiography overnight at 70° C. on an X-ray intensifying screen (Dupont lightning plus, or Picker Max B X-Ray intensifying screen), using pre-flashed film. The X-ray film is developed after 4 hours or on the following day.

For determination with liquid scintillation counting, a positive test (identifying the presence of HBV-DNA in a test sample) is evidenced by retention of CPM (counts per minute) on the 1.2 cm$^2$ sections of the filter. For autoradiography, HBV positive specimens are detected on developed X-ray film as black (darkened) circular spots in the exact positions where the serum samples were originally applied. A preferred method for quantitating the radioactivity in the circular test spots, is to cut them out of the filter matrix with a cylindrical No. 4 cork borer. The cut out spots are then subjected to liquid scintillation spectroscopy.

The following examples are provided to further illustrate the preferred embodiments and advantages of the present invention.

EXAMPLE I

Preparation of a Purified Cloned Labelled HBV-DNA Hybridization Probe (A) Preparation of recombinant plasmid pAO1-HBV.

Plasmid pAO1 was prepared from plasmid pCR1 (see Covey et al, Molec. Gen. Genet 145, 155–158 (1976). Plasmid PCR1 is a derivative of plasmid Col E1 prepared as described in Armstrong et al, Science 196:172–174 (1977) (incorporated herein by reference) by incubating 10 micrograms pCR1 with 10 units of restriction enzyme Pst 1 for six hours at 30° C. in a 100 microliter reaction mixture containing 20 mM Tris HCl pH 7.4, 10 mM MgCl$_2$, 50 mM (NH$_4$)$_2$SO$_4$, and 100 micrograms/ml BSA. After incubation, protein was removed by extraction with phenol, and nucleic acid in the aqueous phase was precipitated by addition of Na acetate pH 5.5 to 0.2M final concentration, followed by the addition of 2.5 volumes of prechilled 100% ethanol. The DNA pellet was resuspended in TE buffer and electrophoresed in a 0.8% agarose slab gel in E buffer for 8 hours. The plasmid band was visualized by ethidium bromide flourescence and the gel portion containing the plasmid band was removed with a scalpel blade. The pAO1 was recovered from the gel by electroelution in a dialysis bag in 2 ml of elution buffer at 200 volts for 30 min at room temperature. The liquid was removed from the bag, adjusted to 0.2M Na acetate, pH 5.5 and 3.0 volumes of prechilled ethanol was added to precipitate nucleic acids. The plasmid was reannealed by dissolving in 100 microliters of reannealing buffer (10 mM Tris HCl pH 7.4; 100 mM NaCl; 1 mM EDTA) and heating to 55° C. for 1 hour, 46° C. for 1 hour, 37° C. for 1 hour and at room temperature for 2 hours. The reannealed plasmid was recovered by ethanol precipitation. The plasmid was dissolved in 10 microliters of ligation buffer (66 mM Tris HCl, pH 7.6, 6.6 mM $MgCl_2$, 10 mM dithiothreitol, 0.4 mM ATP), 0.1 unit of $T_4$ DNA lygase was added and incubation was for 16 hours at 4° C. The religated plasmid (PAO1) was then recovered by phenol extraction and ethanol precipitation.

1.0 micrograms of plasmid pAO1 and 0.3 micrograms of HBV-DNA obtained by SDS-pronase digestion and phenol extraction-ethanol precipitation from Dane particles in which the incomplete viral strand (b strand) had been filled in by the in vitro polymerase reaction, were incubated separately in 1.5 ml plastic conical Eppindorf tubes with restriction enzyme Eco R1 under standard reaction conditions. Each sample was in a 50 ul volume of Tris HCl, pH 7.5, 50 mM NaCl, 5 mM $MgCl_2$ with one unit of Eco R1 for pAO1 or 0.3 units of Eco R1 for Dane particle DNA and incubation was at 37° C. for 6 hours. The reaction mixtures were phenol extracted and the aqueous phases ethanol precipitated. The nucleic acid pellets were resuspended in 50 microliters of TE buffer. 300 nanogram of Eco R1 linearized plasmid and 100 nanograms of Eco R1 linearized, full-length Dane particle DNA (approximately equimolar ratios) were mixed together in a 100 microliters final volume of reannealing buffer and were reannealed under standard conditions. Religation of the annealed plasmid was not performed.

(B) Transformation of bacterial cells for plasmid production

A starter culture of *Escherichia coli* strain HB101 was grown from an agar slant in 20 ml of L-broth suspension medium with 100 micrograms per ml of streptomycin (to prevent overgrowth by contaminating bacteria) overnight at 37° C. with continuous aeration. One ml of culture was transferred to 20 ml of fresh medium and the bacteria were grown to mid log phase (0.8–0.9 OD units at 550 nanometer wavelength) in 3.0 hours. The bacteria were chilled on ice, harvested by centrifugation and washed with 10 mM NaCl. The cells were rendered transformation competent by resuspension in 20 ml of a $CaCl_2$-$MnCl_2$ solution at 4° C. (40 mM Tris HCl, pH 7.4; 100 mM $CaCl_2$; 30 mM $MnCl_2$). The bacteria were placed on ice for 30 min., repelleted, resuspended in 2.0 ml of transformation buffer, and maintained on ice until use (within 2 hours).

Two hundred microliters of the bacterial cell suspension were added to the reannealed, recombinant plasmid and the mixture was incubated at 4° C. for 45 min. Prewarmed L-broth was added to a final volume of 1.0 ml and the mixture was incubated at 37° C. for 20 min. One-tenth ml aliquots were plated on a series of 1.0% agar L-broth plates containing 100 micrograms per ml streptomycin and 25 micrograms per ml kanamycin. The plates were incubated at 37° C. for two days and transformed bacterial colonies were produced. A nitrocellulose filter was laid over the colonies, transferring bacterial material to the filter. The original plates were stored in the refrigerator. The presence of HBV-DNA sequences in transformed colonies (transferred to nitrocellulose filters) was determined by the colony hybridization procedure of Grunstein and Hogness, Proc Natl Acad Sci USA 72:3961–3965 (1975) as outlined below, using $^{32}P$ labelled HBV-DNA prepared from Dane particles by the in vitro "nick translation" reaction. Dane particle DNA labelled by the in vitro polymerase assay can also be used, but the product obtained is of lower specific activity. The filter paper with the bacterial colonies was blotted face up on 0.5M NaOH for 5 min. and was then transferred to two successive Whatmann filter pads containing 1M Tris HCl, pH 7.4. The nitrocellulose filter was then placed on a Whatmann pad containing 1.5M NaCl; 0.5 Tris HCl pH 7.4 for 5 min. and was dried in vacuo for 5 min. Proteinase K solution (1 mg per ml in 0.15M NaCl; 0.015M Na citrate) was added to cover the filter and the filter was incubated for 60 min., washed twice with 0.15M NaCl; 0.015M Na citrate and then with 95% ethanol followed by chloroform. The filter was then dipped in 0.3M NaCl to remove any residual cellular debris and was baked in vacuo at 80° C. for 2 hours. The dry filter was then prehybridized for 6 hours and hybridized at 65° C. for 24 hours under aqueous conditions as described in Table I, using $2 \times 10^6$ cpm heat denatured $^{32}P$ HBV-DNA per filter. After washing the filters at 60° C. to remove unhybridized label, colonies containing HBV-DNA sequences were identified by autoradiography.

Ten colonies containing recombinant plasmids with HBV-DNA sequences were grown in small (5 ml) cultures. Plasmids were isolated from these bacteria by the detergent lysis "cleared-lysate" procedure and were analyzed by restriction enzyme digestion with Eco R1 followed by 0.8% agarose gel electrophoresis using 1 microgram/ml ethidium bromide as a flourescent marker to identify linearized plasmid and HBV-DNA bands. The plasmid has a sequence length of 8700 base pairs and full length HBV-DNA of 3200–3300 base pairs. Bands in these positions were identified by comparison to standard DNA markers of known sequence length. For these experiments, Eco R1 linearized plasmid pBR322 (4380 base prs) and two Hinc II restriction fragments of pBR322 (3256 and 1110 base prs) were used as markers.

(C) Isolation of Purified 3250 base pr HBV-DNA

One plasmid containing an HBV-DNA band in the region of 3250 base prs was selected for large scale preparation. The bacterial colony containing this plasmid was grown overnight in 100 ml of L-broth containing 100 micrograms per ml streptomycin and 25 micrograms per ml kanamycin. This culture was then used to seed four large flasks (2 L) containing 500 ml of L-broth plus antibiotics. The cultures were grown to 0.9 O.D. at 550 nanometers and 100 micrograms per ml chloramphenicol was added to stop bacterial growth and permit plasmid amplification overnight at 37° C. The following morning, the culture flasks were chilled, the bacteria recovered by centrifugation, washed with 10 mM NaCl and resuspended in 25 ml of 25% sucrose (w/v) in 50 mM Tris HCl, pH 8.0. Eight ml of lysozyme (10 mg/ml in 0.25M Tris HCl, pH 8.0) was added and the bacteria were maintained on ice for 5 min. Fifteen ml of 0.25M EDTA, pH 8.0 was added, followed by 5 min of additional incubation on ice. Forty ml of 10% Triton X-100 in 50 mM Tris HCl, pH 8.0; 0.0625M EDTA was added slowly with continued gentle swirling of the solution to produce lysis of the bacteria. The solution was then centrifuged in a Sorvall centrifuge at 30,000 rpm for one hr at 4° C. and the aqueous fraction containing the plasmid was recovered. Solid CsCl (0.9 gm/ml lysate) and ethidium bromide (1 mg/ml lysate from a 10 mg/ml stock solution) were added and the resultant mixture was centrifuged for 48 hrs at 40,000 rpm in a Beckman ultracentrifuge to band the plasmid. After centrifugation, the position of the plasmid band was identified beneath the band of bacterial chromosomal DNA in the middle portion of the gradient by u.v. fluorescence in the dark. The plasmid bands were extracted from the various gradient tubes under direct vision with a u.v. light in the dark by puncturing the side wall of the centrifuge tube with a needle attached to a syringe and withdrawling banded plasmid. Plasmid fractions were pooled and ethidium bromide extracted three times with an equal volume of isopropanol saturated with CsCl. This extraction was important to prevent breakdown of the plasmid by a photofluorescent reaction of the ethidium bromide. The pooled plasmid material was dialyzed against three changes of one liter each of TE buffer in the cold room over 24 hrs. The dialyzed plasmid was phenol extracted, ethanol precipitated and redissolved in one ml TE buffer, recovering 1.2 mg of recombinant plasmid pAO1-HBV.

Fifty micrograms of pAO1-HBV were digested with Eco R1 under standard conditions and the linearized HBV-DNA portion separated from the pAO1 portion by sucrose gradient centrifugation. The 3250 base pr HBV-DNA band recovered from the sucrose gradient was purified further by electrophoresis in a 0.8% agarose gel for 8 hrs at 50 volts in E buffer using 10 micrograms per slot of the gel. The 3250 base pr band was visualized in the gel by ethidium bromide fluorescence and was removed with a scalpel blade. HBV-DNA was electroeluted from the gel fragment and recovered by ethanol precipitation in a yield of 10 micrograms purified homogeneous DNA.

(D) Labelling of purified HBV-DNA

Purified 3250 base pr HBV-DNA was labelled to high specific activity according to the method of Rigby et al., J. Molec Biol 113:237–251 (1977). One ug of HBV-DNA was placed in an Eppindorf tube at 4° C. in a 50 microliter volume of buffer solution containing 50 mM potassium phosphate, pH 7.4, 5 mM $MgCl_2$, 15 uM dAPT and dTTP, and 0.25 mCi each of $\alpha^{32}P$ dGTP and $\alpha^{32}$ dGTP (each at a specific activity of 410 Ci/mM) which had been predried in the tube before the other components were added. One microliter of bacterial DNAse, a 1/10,000 dilution in cold water from a stock of 1 mg per ml, was added with incubation at 23° C. for 1 min, followed immediately by addition of 3.0 microliters (or 12 units) of Pol I (Bohringer/Mannheim) and incubation at 15° C. for several hrs. The labelling of HBV-DNA was followed hourly by removing one microliter of incubation mixture and adding it to a one ml solution of water containing 50 micrograms of carrier salmon sperm DNA. DNA was precipitated in the cold by addition of 100% trichloroacetic acid (w/v) to 10% final concentration, and after 10 min in ice radioactivity in the precipitate was determined by filtration of the sample onto a nitrocellulose filter followed by liquid scintillation spectroscopy. Radioactive nucleotide incorporation into trichloroacetic acid insoluble material increased steadily and after 4 hrs the reaction was stopped by transferring the sample to ice, adding EDTA to a 50 mM final concentration and heating to 65° C. for 5 min. At this point an HBV-DNA specific activity of $3.0 \times 10^8$ cpm per microgram DNA had been achieved. Carrier salmon sperm DNA (50 micrograms) was added to the sample; plus an equal volume of TE buffer containing 0.1M NaCl and 0.1% sodium lauryl sulphate. The sample was then applied to a $0.5 \times 10$ cm column of Sephadex G50 and the labelled DNA separated from residual isotope by gel filtration in the same solution (the labelled DNA appearing in the first effluent from the column). $^{32}P$-HBV-DNA was recovered from the effluent by ethanol precipitation and was stored in 70% ethanol at $-20°$ C. until use. The final amount of recovered labelled HBV-DNA was $1.8 \times 10^8$ cpm.

EXAMPLE II

A 10 milliliter sample of venous blood was collected from a patient, placed in a test tube, and allowed to clot at room temperature. The serum was separated by routine clinical centrifugation at 2,000 RPM in a desktop centrifuge. Five microliters nitrocellulose filter sheet (0.45 micron pore size—Millipore Corporation).

The nitrocellulose filter was air dryed, placed face up on a sheet of Whatmann 3 MM filter paper which was saturated with 0.5M sodium hydroxide for five minutes at room temperature. The filter matrix was then neutralized by transferring to a Whatmann filter paper which was saturated with 1M Tris HCl, pH 7.4 for five minutes. This procedure was repeated and the filter sheet was transferred to a pad of 0.5 molar Tris HCl, pH 7.4; 1.5 molar NaCl for 5 minutes and then dryed in a vacuum oven at room temperature for five minutes. After removal from the oven, the filter sheet was immersed in a shallow dish containing 50 ml of a protein digestion solution containing 0.2 mg of pronase per ml, 0.3M sodium chloride and 0.03M sodium citrate, pH 7.0 for 60 minutes at 37° C. After removal from the dish, the spot to which the serum specimen had been applied was no longer visible.

The filter was washed gently by dipping it into two successive pans containing an aqueous solution of 200 ml of 0.3M sodium chloride, 0.03M sodium citrate and air dried at room temperature. After rewashing with the preceding solution, the filter was again dried in a vacuum oven at 80° C. for two hours and placed in a heat sealable polyethylene plastic bag capable of withstanding immersion in boiling water. Ten ml of an aqueous prehybridization solution (formula as in Table I) was added, the bag was sealed and the contents incubated in a water bath at 65° C. for six hours.

The prehybridization solution was removed from the bag and replaced with 10 ml of fresh aqueous hybridization solution, identical to the prehybridization solution, except that the concentrations of polyvinylpyrolidone, Ficoll and albumin were reduced to 0.02% V/V, 0.02% V/V and 0.02% W/V, respectively. $2 \times 10^7$ cpm of $^{32}P$ HBV-DNA prepared as in Example 1 were dissolved in 50 microliters TE buffer and boiled at 100° C. for 5 min, chilled rapidly on ice and added to the contents of the bag. The bag was resealed and incubated overnight at 65° C. After the radioactive waste solution was discarded, the filter was removed from the bag, and washed twice for five minutes in a solution of 0.3M NaCl, 0.03M sodium citrate and 0.1% sodium lauryl sulphate at room temperature. The filter was then washed twice with a solution containing 0.015M sodium chloride, 0.0015M sodium citrate and 0.1% sodium lauryl sulphate for 30 minutes at 60° C. and dried.

The dry filter matrix was exposed to autoradiography overnight at −70° C. against a Dupont lighting plus intensifying screen, and the X-ray film developed the following day. The sample (obtained from a known HBV-DNA carrier) was positive as shown by the presence of a black circular spot on the filter in the location on which the serum sample had originally been deposited. The HBV-DNA probe employed consisted of purified HBV-DNA which had been cloned in plasmid pAO1, reisolated as a 3250 base pair molecule and labelled by "nick translation" with $^{32}P$ dCTP and $^{32}P$ dGTP to a specific activity of $3 \times 10^8$ CPM per microgram DNA.

EXAMPLE III

Ten ul samples of serum from patients known to be positive for $HB_sAg$ by radioimmunoassay and negative controls were tested by the filter hybridization method of the present invention for the presence of HBV-DNA. The same technique and reagents were employed as in examples I and II. The autoradiogram was developed after 4 hr exposure at −70° C. with Dupont intensifier screens and preflashed film, and showed positive results in all $HB_sAg$ carriers, but not in controls. Table I illustrates results obtained by liquid scintillation spectroscopy of five circular areas (0.5 cm diameter) of the filter sheet where serum samples were applied and a 1 cm² blank section.

| Sample | HBsAg (RIA) | HBV-DNA (cpm) |
|---|---|---|
| 1 | − | 1 |
| 2 | + | 134 |
| 3 | + | 447 |
| 4 | + | 208 |
| 5 | + | 78 |
| 6 | 1.0 cm² Blank Square Section | 9 |

(cpm = counts per minute)

EXAMPLE IV

Serum specimens from chimpanzees were tested for five hepatitis B viral protein markers by radioimmunoassay and for the presence of HBV-DNA by the filter hybridization test of the present invention. Initial experiments using the same process as in Example II, but with a crude hybridization probe consisting of $^{32}P$ labelled recombinant pAO1 plasmid containing inserted HBV-DNA, showed hybridization with chimpanzee DNA regardless of whether the chimpanzees were, or were not, HBV-carriers. Therefore, all subsequent studies utilized repurified 3250 base pair HBV-DNA as prepared in Example I. Table A illustrates the results of radioimmunoassay studies and correlation with HBV-DNA identification in serum by the filter hybridization test. Five chimpanzees who were positive for HBsAg were also positive for anti-HBc, HBeAg and HBV-DNA. All of the other chimpanzees, including some who had previous HBV infection and were cured (anti HBs, anti-HBc, and/or anti HBe positive) and others who were not exposed to HBV (negative for all markers), were negative for HBV-DNA in their serum.

TABLE A

| Identification No. | Chimpanzee | | | | | |
| | HBsAg | Anti-HBs | Anti-HBc | HBeAg | Anti-HBe | HBV-DNA |
|---|---|---|---|---|---|---|
| 21 | − | − | + | − | − | − |
| 30 | + | + | + | + | − | + |
| 31 | + | − | + | + | − | + |
| 55 | − | + | + | − | + | − |
| 116 | + | − | + | + | − | + |
| 125 | + | − | + | + | + | + |
| 319 | − | − | + | − | − | − |
| 323 | + | − | + | + | + | + |
| 336 | − | − | + | − | − | − |
| 342 | − | − | − | − | − | − |
| 644 | − | + | + | − | + | − |

Legend:
− Negative
+ Positive

EXAMPLE V

A group of human specimens were tested for the presence of HBV-DNA by the filter hybridization test. Samples that were positive for HBsAg and HBeAg were positive for HBV-DNA. Serum from patients who were positive for only HBsAg were negative for HBV-DNA. A concentrated preparation of Dane particles was strongly positive for HBV-DNA; however, serum from one HBsAg-HBeAg carrier (a renal dialysis patient) was 5–10 times stronger in the hybridization reaction than the Dane particle concentrate indicating that serum from this patient was highly infectious. Samples from patients who were positive for anti HBc but no other marker (chronic anti HBc carriers) were negative for HBV-DNA. Two lots of HBsAg vaccine in preparation for human trials were weakly positive for HBV-DNA, and DNA extracts from human hepatocellular carcinomas and liver tissue from HBsAg carriers were positive for HBV-DNA. The test results are summarized in Table B.

TABLE B

| Sample (Patient ID) | HBsAg | Anti HBs | Anti HBc | HBeAg | Anti HBe | HBV-DNA |
|---|---|---|---|---|---|---|
| 1. I.H. | + | + | + | + | − | + |
| 2. W.O. | + | N.D. | + | + | − | + |
| 3. M.R. | + | + | + | + | − | + |
| 4. E.G. | + | − | + | + | − | + |
| 5. J.R. | + | − | + | + | − | + |
| 6. "Dane" | + | − | − | + | − | + |
| 7. J.G. | − | + | + | − | + | − |
| 8. E.E. | − | − | − | − | − | − |
| 9. P.P. | − | + | + | − | + | − |
| 10. W.T. | − | − | + | − | − | − |
| 11. W.P. | + | − | + | − | + | − |
| 12. S.D. | − | − | − | − | − | − |
| 13. C.M. | − | + | + | − | + | − |
| 14. M.Y. | − | − | − | − | − | − |
| 15. H.G. | + | − | + | − | − | − |
| 16. C.R. | − | + | N.D. | − | + | − |
| 17. B.G. | − | − | − | − | − | − |
| 18. A.B. | + | − | + | − | + | − |
| 19. B.C. | − | + | − | − | − | − |
| 20. M.E. | − | + | + | − | + | − |
| 21. 05-0051 | − | − | + | − | − | − |
| 22. 05-0051 | − | − | + | − | − | − |
| 23. 05-0066 | − | − | + | − | − | − |
| 24. 05-0079 | − | − | + | − | − | − |
| 25. C-152 | − | − | + | − | − | − |
| 26. C-215 | − | − | + | − | − | − |
| 27. C-462 | − | − | + | − | − | − |

TABLE B-continued

| Sample (Patient ID) | HB$_s$Ag | Anti HB$_s$ | Anti HB$_c$ | HB$_e$Ag | Anti HB$_e$ | HBV-DNA |
|---|---|---|---|---|---|---|
| 28. C-490 | − | − | + | − | − | − |
| 29. C-501 | − | − | + | − | − | − |
| 30. C-542 | − | − | + | − | − | − |

It should be recognized that the present test is a direct assay in which the sample of the patient's blood (serum) or other peripheral fluid is applied to a nitrocellulose filter without pretreatment of any sort. Molecular hybridization was performed with an HBV-DNA probe comprised of cloned and repurified HBV-DNA that carries a radioactive label. An important aspect of the test is the ability to recognize any nucleotide sequence or fragment in the test sample that is at least about 200 base pairs in length or longer (and which corresponds to a portion of the purified DNA in the probe). The test is approximately 1000 times more sensitive than radioimmunoassay, and is suitable for mass screening of potential subjects. The use of purified, recombinant HBV-DNA virtually eliminates the possibility of obtaining false postive results with serum, thereby increasing the reliability of the test as a screening device for large populations.

What is claimed is:

1. A method for detecting the presence of hepatitis B virus in a test specimen containing at least a portion of the DNA sequence of the hepatitis B virus consisting essentially of
    affixing the test specimen suspected to contain said hepatitis B virus DNA directly on a substrate,
    incubating the test specimen in contact with a reagent comprising cloned hepatitis B virus DNA containing label for detecting the presence of said cloned DNA, said hepatitis B virus DNA having been purified by reisolation from a cloning vector,
    treating said substrate bearing the affixed test specimen with a solution which digests all protein while leaving the nucleic acid affixed to said substrate, prior to conducting said incubating step,
    conducting said incubation under conditions which permit the labelled purified, cloned hepatitis B virus DNA to combine with the unlabelled hepatitis B virus DNA of the test specimen,
    removing uncombined purified hepatitis B virus DNA from the substrate, and
    reading the substrate to detect the presence of said label.

2. The method of claim 1 which comprises detecting a hepatitis B virus DNA sequence comprising at least about 200 nucleotide base pairs.

3. The method of claim 1 wherein said reagent comprises a hepatitis B virus DNA sequence containing at least about 200 nucleotide base pairs.

4. The method of claim 1 wherein said solution comprises a protein digesting enzyme.

5. The method of claim 1 which comprises denaturing the labelled, cloned hepatitis B virus DNA to form single strands of said labelled, cloned hepatitis B virus DNA prior to said incubating step.

6. The method of claim 1 which comprises denaturing said test specimen on the substrate to form single DNA strands prior to said incubating step.

7. The method of claim 1 which comprises placing said test specimen directly on said substrate without prior purification of said test specimen.

8. The method of claim 1 wherein the test specimen is an aqueous solution or suspension of a biological material.

9. The method of claim 8 wherein the substrate comprises a solid matrix.

10. The method of claim 8 wherein said predetermined conditions comprise a predetermined time period and a predetermined temperature.

11. The method of claim 8 wherein the test specimen comprises a member selected from the group consisting of blood, blood products, serum and peripheral body fluids.

12. The method of claim 11 wherein said test specimen comprises blood serum derived from a human subject.

13. The method of claim 9 wherein said solid matrix comprises a nitrocellulose filter.

14. The method of claim 13 wherein said label comprises a radioactive substance.

15. The method of claim 14 wherein said radioactive label substance comprises $^{32}P$.

16. The method of claim 14 wherein said radioactive label comprises $^{125}I$.

17. The method of claim 13 wherein said label comprises a fluorescent or an immunofluorescent substance.

18. The method of claim 12 wherein said substrate comprises a modified cellulosic paper comprising a sheet or web of cellulose fibers substituted with diazotized metaaminobenzyloxymethyl for covalent binding thereto of nucleic acid residues.

19. The method of claim 10 wherein said predetermined time period is between about 8 and 36 hours.

20. The method of claim 10 wherein said predetermined temperature is between about 5 and 10 degrees C. below the melting temperature of said HBV-DNA.

21. The method of claim 20 which comprises performing said incubation step in the presence of a hybridization solution.

22. The method of claim 21 which comprises conducting said incubation in a sealed container.

23. The method of claim 22 wherein said hybridization solution comprises an aqueous salt solution between 3 and 6 times SSC and having a pH in the range between about 6.5 and 8.0, said solution also containing denatured carrier DNA.

24. The method of claim 22 wherein said hybridization solution comprises a partially organic solution containing formamide.

25. The method of claim 13 wherein said label is bioluminescent.

26. A method for the detection of a known DNA sequence comprising at least about 200 nucleotide base pairs in a biological sample consisting essentially of
    affixing a biological sample to be tested for the presence of said known DNA sequence to a substrate,
    treating said substrate bearing said sample to remove all protein thereon and to leave nucleic acid affixed to said substrate,
    contacting said sample with a hybridization probe comprising cloned DNA containing said sequence, said cloned DNA having been repurified by reisolation from a cloning vector, said purified DNA including a detectable label,
    incubating said probe in contact with said sample under hybridization conditions which permit the labeled DNA to hybridize with only DNA containing said nucleotide sequence, removing from said substrate the labeled DNA that has not hybridized with the DNA in said sample, and analyzing said substrate for the presence of said label.

27. The method of claim 26 wherein said hybridization probe contains at least about 200 nucleotide base pairs.

28. The method of claim 26 wherein said protein removal treating step comprises immersing said substrate in a solution containing a protein digesting enzyme.

29. The method of claim 26 wherein said known DNA sequence comprises hepatitis B virus DNA of about 3,250 base pair length.

30. The method of claim 29 wherein said hybridization conditions comprise conducting said incubation in the presence of a solution having a pH of about 7.0, said solution being between about 3 and about 6 SSC and containing denatured carrier DNA.

31. A method for identifying a human carrier of hepatitis B virus consisting essentially of collecting a blood specimen from a suspected carrier of said hepatitis B virus, isolating the serum from said specimen, applying between about 5 and about 200 ml of said serum absent any DNA purification pretreatment to a filter matrix made of a material that will bind RNA and DNA, treating said matrix bearing said serum to remove all protein thereon, placing said substrate in a sealable container with a predetermined quantity of an aqueous hybridization solution of between 3 and 6 times SSC and approximately neutral pH, and a probe prepared by cloning hepatitis B virus DNA, purifying the cloned hepatitis B virus DNA by reisolation from the recombinant plasmid and labelling the reisolated DNA to high specific activity, sealing the container, incubating the sealed container for between about 8 and 36 hours at a temperature between 65° and 68° C. to permit the labelled hepatitis B virus DNA to combine with any hepatitis B virus DNA present in said serum, removing uncombined DNA from the presence of said substrate, and analyzing the substrate for the presence of said radioactive label using liquid scintillation spectroscopy or autoradiography.

32. A diagnostic test kit for detecting the presence of hepatitis B virus DNA consisting essentially of a diagnostic reagent, comprising highly purified, cloned, reisolated hepatitis B-virus-DNA, labelled to a high specific activity, a sealable container constructed of a material capable of withstanding boiling water temperatures and a matrix material capable of adhering DNA or RNA thereto.

33. The diagnostic test kit of claim 32 wherein said matrix material is nitrocellulose filter paper.

34. The diagnostic test kit of claim 32 wherein said matrix material is diazobenzyloxymethyl-cellulose paper.

35. The diagnostic test kit of claim 33 further comprising a hybridization solution having a pH between pH 6.5 and pH 8.0, said solution being between 3 and 6 times SSC and containing denatured DNA salmon sperm or calf thymus.

36. The diagnostic test kit of claim 33 further comprising a partially organic hybridization solution containing formamide.

* * * * *